United States Patent
Hamilton

(10) Patent No.: US 6,280,184 B1
(45) Date of Patent: Aug. 28, 2001

(54) METHOD AND APPARATUS FOR REMOVING BONDED DENTAL APPLIANCES

(76) Inventor: David C. Hamilton, Forrest Rd. R.D. 3, New Castle, PA (US) 16105

( * ) Notice: Subject to any disclaimer, the term of this patent is extended or adjusted under 35 U.S.C. 154(b) by 0 days.

(21) Appl. No.: 09/526,740

(22) Filed: Mar. 16, 2000

(51) Int. Cl.[7] .................................................. A61C 3/00
(52) U.S. Cl. .................................................. 433/4; 433/159
(58) Field of Search ............................. 433/4, 159, 160, 433/9

(56) References Cited

U.S. PATENT DOCUMENTS

| | | | |
|---|---|---|---|
| 354,863 | 12/1886 | Hughes | 433/160 |
| 831,307 | 9/1906 | Spahn | 433/156 |
| 908,056 | 12/1908 | Whitnry et al. | 433/160 |
| 1,007,824 | 11/1911 | Trosper | 433/160 |
| 1,628,499 | 5/1927 | Joesch | 433/160 |
| 2,698,483 | 1/1955 | Berkowitz | 433/156 |
| 3,146,804 | 9/1964 | Wallshein | 433/160 |
| 3,755,902 | 9/1973 | Northcutt | 433/4 |
| 3,986,265 | 10/1976 | Cusato | 433/4 |
| 4,248,587 * | 2/1981 | Kurz | 433/4 |
| 4,752,220 | 6/1988 | Dietrich | 433/1 |
| 5,269,680 * | 12/1993 | Kawaguchi | 433/9 |
| 5,366,372 | 11/1994 | Hansen et al. | 433/4 |
| 5,833,460 | 11/1998 | Maeda | 433/159 |

FOREIGN PATENT DOCUMENTS 0942733   7/1982   (SU).

* cited by examiner

Primary Examiner—John J. Wilson
(74) Attorney, Agent, or Firm—Kenyon & Kenyon

(57) ABSTRACT

An orthodontic onlay having a mesial and distal sections is debonded from multiple teeth by positioning a plier-type debonding apparatus having a first and a second lever arms pivotally connected for rotation relative to each other and having respectively a first and a second handle portions, a hook extending from said second jaw portion, and a bracing platform pivotally connected to said first jaw portion and facing the hook. The appliance is removed by engaging the hook at the adhesive line of the appliance and the tooth, placing the bracing platform against the occlusal bonded surface of the appliance, pivoting the debonding apparatus clockwise and counterclockwise.

15 Claims, 2 Drawing Sheets

METHOD AND APPARATUS FOR REMOVING BONDED DENTAL APPLIANCES

BACKGROUND OF THE INVENTION

1. Field of the Invention

The present invention relates to an apparatus for removing dental appliances bonded to multiple teeth and a method for using the same. More specifically, the present invention relates to an apparatus for removing bonded dental appliances having a stationary hook and a unique platform to engage the flat surface of the acrylic covering the teeth.

2. Brief Description of the Background Art

Orthodontics appliances, also known as acrylic onlays, are either bonded or removable intra-oral devices which alter the posture of the maxilla and mandible (jaws) and the muscle forces against the teeth and the crano-facial skeleton. These devices are molded to fit the patient specific plaster or stone models of the patient's upper or lower teeth and dento-facial specifications and are placed in the mouth for a finite duration to dynamically alter the jaw's neuromuscular action thereby affecting bony growth and occlusal relationships.

In general, acrylic appliances are used for orthopedic correction, functional correction and disarticulation of the teeth and jaws. In orthopedic correction, also known as skeletal correction, the appliance functions to change the size and skeletal position of the jaws. In functional treatment, the appliance causes the jaw to close into a new position, thereby enabling the jaw to modify its growth and assume a new posture. This procedure is often used to permit the jaw to reposture and the temporomandibular joint to modify in order to improve facial/skeletal appearance and alleviate pain associated with TMD or Temporo-Mandibular Joint Disorders or Dysfunction. These applications have made acrylic appliances indispensable to dentistry.

The apparatus specific to this invention is used for removal of the bonded appliances. The advantage of the bonded appliances primarily relates to the elimination of patient compliance with wearing of the removable appliances and guarantees 24-hour per day functional change.

Because of their particular application, the ideal age for starting treatment is between the ages of three to 12 years. That is, the age where the cranial structure is still growing and could adapt to the new posture. The acrylics are bonded (cemented) to the teeth using an adhesive for a finite treatment period. The patient is unable to alter the position of the appliance until it is removed by the orthodontist. At the end of the treatment period the practitioner removes the acrylic appliance by breaking the bond and ideally recovering the appliance intact. Thereafter, the appliance may be used as a temporary onlay until a stabilizing plate or retainer is properly fitted to the patient. The retaining appliance may be worn for a shorter period of time (e.g., overnight) to supplement the treatment.

Removing the bonded acrylic has been a source of great distress and some discomfort to the patients and especially to the younger patients. Also, because the appliance is often used as a temporary onlay after it is removed, its intact preservation during the removal stage is a source of distress to the practitioners who must not fracture or otherwise damage the appliance during removal. Patient comfort and reducing the time taken to remove the appliance are important factors. In addition, removing the appliance without causing laceration of the gingival tissue is important to both the patient and the practitioner. Finally, because of the above-stated factors, orthodontists are reluctant to relegate this seemingly routine task to dental auxiliaries.

Although various devices for extracting tooth or synthetic onlays such as caps and bridges have been proposed, none addresses the particular problems associated with removing acrylic appliances. For example, U.S. Pat. No. 354,863 discloses a pair of dental forceps for extracting roots of teeth. The extraction device comprises a pair of pivotally connected arms that form the jaws of the forceps at one end, and the arms of the forceps at the other end. The jaws include a convex-shaped metal disc that is rotatably connected to the forceps by a ball joint, and a beak that sits perpendicular to the face of the metal disc. The beak has a hallow-ground center enabling it to fit upon the root of the tooth. This device is not suitable for removing acrylic appliances. Particularly, the convex shape of the metal disc prevents a snug bracing of the acrylic surface. Instead, it would concentrate the force exerted by the forceps in a relatively small area which could cause fracture of the appliance. In addition, the sharp narrow beak would create a very small contact area with the acrylic that could also fracture the appliance.

U.S. Pat. No. 1,628,499 discloses a device for tooth extraction. The device comprises a scissors-like forceps having as a first jaw a pivotally mounted rubber-covered disc adapted to rest against the gum, and a second jaw that impinges on the back face of the tooth. The second jaw is described as having a shank which connects to the jaw at one end and forms a concave angular recess which converges to a pointed tip at the other end. The concave recess allows for the device to come close to the cusp of the tooth while not making contact therewith. In practice, the device is used by placing the rubber-covered disc against the outer gum and impinging the upper pointed tip of the shank against the inner surface of the tooth. This device is also not suitable for removing an acrylic onlay because the pointed tip does not allow for a proper gripping of the acrylic. Instead, it would cause bleeding as the beak would cut against the gingival tissues. Moreover, the pointed tip of the beak is designed for securing and extracting teeth and it would not establish a proper grip on the acrylic. As with the Hughes patent, this device would also fracture the appliance.

U.S. Pat. No. 3,755,902 to Northcutt discloses a tool for removing a very small orthodontic onlay which has been cemented to the tooth. Northcutt's device comprises a pair of scissors-like jaws connected to a lever. The upper jaws have forward-intruding portion which goes behind the onlays surface to separate the onlay from the tooth surface. The lower jaw comprises a stationary pad enabling the edge of the tooth to rest thereon. This device is also not suitable for removing acrylic onlay because it would be uncomfortable to the patient, endanger both the tooth enamel and structure and could severely lacerate the gingival tissues.

Two of the above structures are variations of a dental forceps designed for extracting teeth. Because they are designed to fit a human structure and remove a tooth, they do not lend themselves to non-destructive removal of acrylic appliances. The third for debonding very small (less than 4.0 mm) attachments bonded to individual teeth. Therefore, it is desirable to provide a simple device for debonding an acrylic appliance wherein the device is capable of non-destructive removal of the appliance with minimal trauma and injury to patient.

SUMMARY OF THE INVENTION

Accordingly, it is an object of the present invention to provide a debonding device that allows for efficient and comfortable removal of an acrylic appliance. It is also an object of the present invention to provide a device that enables the removal of the dental appliance with minimal discomfort or trauma to the patient while preventing damage to the tooth structures and the gingival tissues. A further object of the present invention is to provide a simple mechanical device that enables non-destructive removal of the appliance.

These and other objectives are achieved by employing a device for removing bonded acrylic appliances comprising a first and a second lever arms pivotally joined for rotation relative to each other and having a first and a second handle portions and a first and a second jaw. The first jaw having a pivoting bracing platform which enables it to adjust to various appliance shapes and to rest snugly against the occlusal surface of the appliance, while the second jaw having a broad hook-shaped projection engages the gingival area of the appliance. Once properly engaged, rotation of the operator's hand clockwise and counterclockwise with moderate force physically breaks the bonding.

BRIEF DESCRIPTION OF THE DRAWINGS

The various features of the invention will best be appreciated by simultaneous reference to the description which follows and the accompanying drawings, in which.

DETAILED DESCRIPTION OF THE INVENTION

Figure 1:
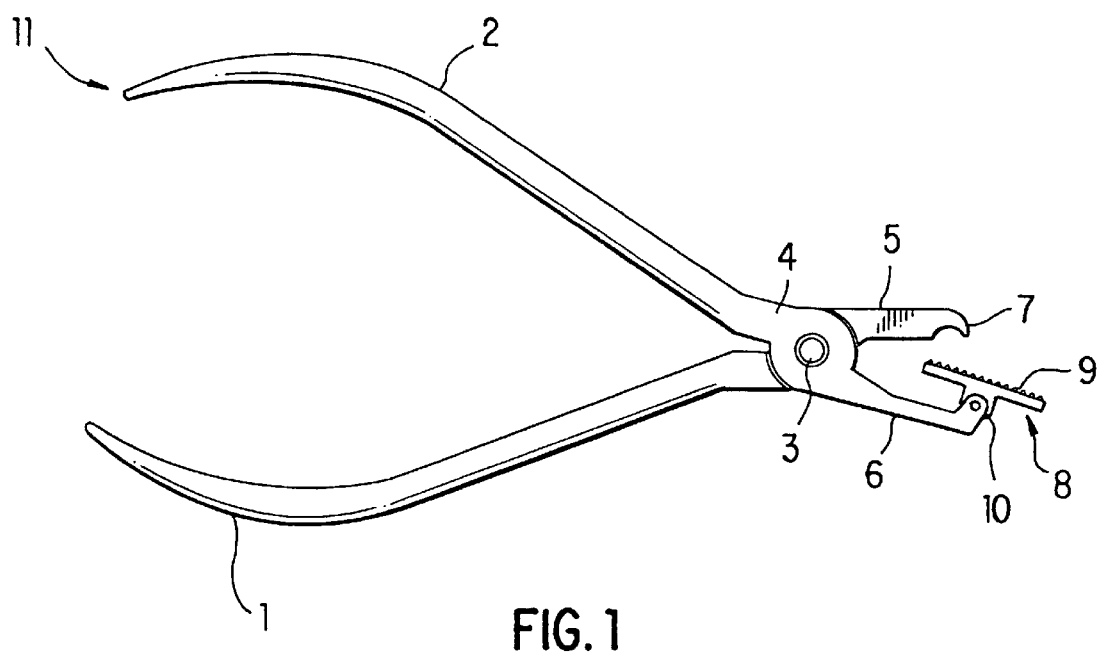
FIG. 1 schematically represents a plan view of a first embodiment of the apparatus for removing bonded dental appliances of the present invention.

FIG. 1 represents the first embodiment of the present invention. Referring to FIG. 1, the debonding apparatus 11 of the first embodiment of the present invention is shown to include a first and a second elongated grip handles 1 and 2, pivotally connected by pivot pin 3. Members 5 and 6 extend from the pivot area 4 and form the first and second jaws respectively. Hook 7 is integrally connected to the first jaw portion 5, forming an arch such that the tip of the hook faces the surface of the bracing plat form 8. Hook 7 could also be manufactured such that it is removably engaged to the jaw portion 5. In a preferred embodiment, hook 7 extends from the first jaw portion 5 and makes a right angle with the longitudinal access of the first jaw portion. This angle could be modified to accommodate different applications. In addition, in a preferred embodiment hook 7 is shaped such that the tip area of the hook does not extend beyond the plane of the first jaw portion 5. The recess portion just below the hook is configured to allow for engaging the acrylic appliance without contacting the tooth or lacerating the gingival tissues. Therefore, the recess portion of the hook 7 is configured to have a radius of curvature large enough to would allow such a clearance.

In a preferred embodiment, hook 7 has a broad, flat surface that enables it to engage the adhesive line where the acrylic appliance is bonded to the tooth. The broad contact line enables the hook to properly engage the appliance at the adhesive line without lacerating the gum tissue or concentrating the contact force on a small area thereby damaging the appliance.

Figure 2:
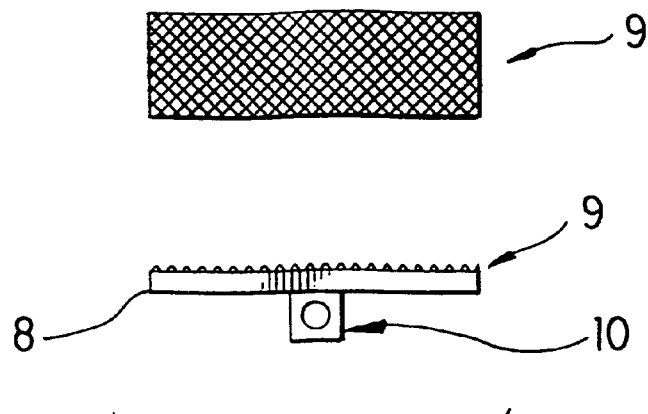
FIG. 2 represents the bracing platform of the second jaw portion including the serrated bracing surface.

Referring to FIG. 2, the bracing platform 8 is pivotally connected to the second jaw portion 6 (FIG. 1) via pivoting means 10, preferably a pivoting lug. The pivoting means 10 allows the apparatus to transfer a broad application of the force and the practitioner's wrist motion to the appliance, automatically adjusting to the position of the occlusal tooth coverage of the apparatus. Platform 8 is preferably rectangular, but it could be modified to suit the practitioner's application. On the exposed surface, the bracing platform 8 forms a flat surface covered by the gripping surface 9. The gripping surface 9 preferably has a serrated surface which conforms to the occlusal surface of the acrylic appliance when the apparatus is engaged. This provides a firm, yet gentle, grip of the appliance. Also the flat, broad rectangular gripping surface 9 distributes the force throughout the contact surface thereby preventing chipping or fracturing the acrylic.

Figure 3:
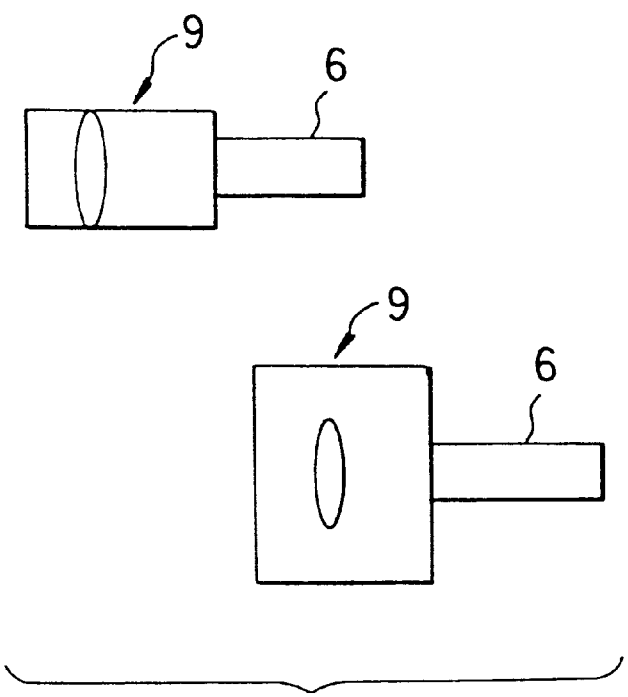
FIG. 3 represents two embodiments illustrating the rotation of the pivoting platform.

FIG. 3 represents a second embodiment of the present invention. In this embodiment, the bracing platform 8, which is connected to member 6 has been rotated 90 degrees about the pivoting means 10. The two alternatives enable the gripping surface to be adjusted to suit different applications or different appliance configurations.

The grip handles 1 and 2 are spaced apart from each other so that the angular movement of the grip handles about the pivot could be more accurately controlled or so that the device could fit better in the practitioner's hand. The handle grips could be modified to have a different curvature, or alternatively have no curvature.

Material of construction could be any commonly known material which could be sterilized in accordance with the OSHA standards. For example, the entire apparatus could be made of stainless steel. Alternatively, carbide steel could be used as an insert for a hook portion that is engaged to stainless steel jaws.

The use of the apparatus is universal. That is, it can be applied to the lower or the upper jaw, left or right, as well as to the mesial or the distal ends of the appliance. In a preferred mode of application, the practitioner opens the apparatus and places hook 7 against the edge of the acrylic appliance adjacent to the alveolar tissues (the gum tissues abutting the enamel of the tooth). If applied to the upper jaw, the hook should engage the acrylic appliance just below the gum line. Conversely, if applied to the lower jaw, the hook should be placed just above the gum lines. The recess of the jaw portion 5 provides a clearance which enables hook 7 to sit over the acrylic without contacting the gingival tissues. The bracing platform 8 is then placed against the occlusal surface of the appliance such that the gripping surface 9 firmly embraces the occlusal surface of the acrylic. When the apparatus is manipulated the platform engages the flat surface of the occlusal acrylic, giving it stability and strength. In this manner, the force of the apparatus is distributed throughout the gripping surface 9 of the bracing platform 8 preventing damage to the appliance. Once a proper grip has been established, the practitioner rotates the apparatus clockwise and counter clockwise in an effort to loosen and break the adhesive bond. The inter-face of adhesive with the tooth is far less strong than the enamel of the surface of the tooth and the inter-face breaks in response to the force applied by the debonding apparatus 11.

If the bond does not break following the first attempt, the apparatus could be moved distally (away far from the middle) and the procedure repeated.

While in the above embodiment the bracing platform is engaged after the hook is properly positioned, it would be obvious to those skilled in the art that the reverse of this procedure (i.e., engaging the bracing platform before positioning the hook) is also viable. However, it must be noted that the first method is less traumatic to the patient in that laceration of the gum tissue is less likely.

As yet another alternative, the practitioner could start by engaging the apparatus at the distal end of the jaw and work toward the mesial end. It is understood that any other variation in applying the device is within the scope of this invention.

Several different pliers variations might be made available. The primary difference would be the shape and size of the pivoting platform and its relationship to the hinge connecting it to the pliers. It would be understood to one of ordinary skill in the art that these variations are within the intended scope of the present invention.

I claim:

1. An apparatus for removing bonded orthodontic appliances comprising:

a first lever arm and a second lever arm pivotally joined for rotation relative to each other and having respectively a first handle portion and a second handle portion defining the lever arms' proximal ends and a first and a second jaw portions defining the lever arms' distal ends, a hook extending from said second jaw portion, said hook having a broad flat engaging surface for engaging an adhesive line of an appliance bonded to the tooth, a bracing platform pivotally connected to said first jaw portion.

2. The apparatus of claim 1, wherein said hook has a sharpened portion extending therefrom.

3. The apparatus of claim 1, wherein said hook has a planar surface.

4. The apparatus of claim 1, wherein said hook is removable from said first jaw portion.

5. The apparatus of claim 1, wherein said bracing platform further comprises at least one gripping surface.

6. The apparatus of claim 5, wherein the gripping surface is serrated.

7. The apparatus of claim 1, wherein the bracing platform has a rectangular shape.

8. The apparatus of claim 1, wherein said hook is a projection of the first jaw portion in a direction perpendicular to said bracing platform.

9. The apparatus of claim 1, wherein said second jaw portion further comprises a recess portion.

10. A method for removing a bonded acrylic appliance comprising:

(a) providing an apparatus for removing bonded orthodontic appliances having (i) a first lever arm and a second lever arm pivotally joined for rotation relative to each other and having respectively a first handle portion and a second handle portion defining the lever arms' proximal ends and a first jaw portion and a second jaw portions defining the lever arms' distal ends, (ii) a hook extending from said first jaw portion, (iii) a bracing platform pivotally connected to said first jaw portion, (b) engaging said hook against the bonded edge of the acrylic appliance, (c) placing said bracing platform against the occlusal surface of the acrylic appliance, and (d) removing the acrylic appliance.

11. The method of claim 10, wherein the bracing platform is rectangular.

12. The method of claim 10, wherein the first jaw portion further comprises a recess portion.

13. The method of claim 10, wherein said hook has a planar surface.

14. The method of claim 10, wherein said hook further comprises a sharpened portion extending therefore.

15. The method of claim 10, wherein said bracing platform is serrated.

* * * * *